United States Patent [19]

Hale et al.

[11] Patent Number: 5,328,028
[45] Date of Patent: Jul. 12, 1994

[54] HAZARDOUS WASTE DISPOSAL METHOD AND DRUM ASSEMBLY

[75] Inventors: James A. Hale, Red Bank; Jean Sawyer, Westfield; John A. Plunkett, Wyckoff; Lou A. Marinaccio, Highlands, all of N.J.

[73] Assignee: Greif Bors. Corporation, Delaware, Ohio

[21] Appl. No.: 108,927

[22] Filed: Aug. 18, 1993

Related U.S. Application Data

[63] Continuation of Ser. No. 2,121, Jan. 7, 1993, abandoned, which is a continuation of Ser. No. 675,130, Mar. 25, 1991, abandoned, which is a continuation of Ser. No. 397,541, Aug. 22, 1989, abandoned.

[51] Int. Cl.⁵ .............................................. B65D 83/10
[52] U.S. Cl. ................................... 206/366; 206/370; 220/404; 220/908; 588/258
[58] Field of Search ............... 206/364, 365, 366, 370, 206/496, 136, 482.4, ; 220/908, 253, 256, 259, 254, 404, 257; 252/628, 633; 250/506.1; 100/137, 215, 227, 228, 245, 246, 295; 184/14.1, 24, 38.1, 105.2; 4/315, 351, 420, 459, 458; 558/258

[56] References Cited

U.S. PATENT DOCUMENTS

| | | |
|---|---|---|
| 2,123,712 | 7/1938 | Clark .................................. 184/38.1 |
| 2,961,399 | 11/1960 | Alberti ............................... 252/628 |
| 3,605,129 | 9/1971 | Ellis et al. ............................. 4/459 |
| 3,632,038 | 1/1972 | Souza ................................. 220/908 |
| 3,965,900 | 6/1976 | Boedecker ......................... 604/350 |
| 4,058,479 | 11/1977 | White et al. ........................ 252/633 |
| 4,077,493 | 3/1978 | Spaude et al. ...................... 184/38.1 |
| 4,083,428 | 4/1978 | Ness .................................. 184/105.2 |
| 4,298,144 | 11/1981 | Pressl ................................ 184/105.2 |
| 4,331,074 | 5/1982 | Behman ............................... 100/215 |
| 4,390,040 | 6/1983 | Beyen ................................. 137/440 |
| 4,430,084 | 2/1984 | Deaton ............................... 604/317 |
| 4,534,489 | 8/1985 | Bartlett ............................... 220/404 |
| 4,594,513 | 6/1986 | Suzuki et al. ...................... 252/633 |
| 4,598,838 | 7/1986 | Zakrajsek .......................... 220/404 |
| 4,599,518 | 7/1986 | Schmidt et al. ................... 250/507.1 |
| 4,647,213 | 3/1987 | Hay .................................... 366/199 |
| 4,717,510 | 1/1988 | James ................................. 252/633 |
| 4,760,783 | 8/1988 | Torita et al. ........................ 100/137 |
| 4,761,127 | 8/1988 | O'Brien et al. ..................... 425/110 |

Primary Examiner—Donald P. Walsh
Assistant Examiner—Anthony R. Chi
Attorney, Agent, or Firm—Kane, Dalsimer, Sullivan, Kurucz, Levy, Eisele & Richard

[57] ABSTRACT

A drum assembly for the collection and disposal of hazardous waste includes an enclosure with an access hole for collecting the waste. After the waste has been collected, the drum is opened and an insert is positioned to cover the access hole. The drum is then closed to form a sealed container.

16 Claims, 4 Drawing Sheets

HAZARDOUS WASTE DISPOSAL METHOD AND DRUM ASSEMBLY

This is a continuation of copending application Ser. No. 08/002,021 filed on Jan. 7, 1993 (abandoned) which is a continuation of copending application Ser. No. 07/675,130 filed on Mar. 25, 1991 (abandoned) which is a continuation of copending application Ser. No. 07/397,541 filed on Aug. 22, 1989 abandoned.

BACKGROUND OF THE INVENTION a. Field of Invention

This invention pertains to a method and a drum for collecting and disposition of hazardous waste materials, and more particularly to method utilizing a drum assembly which includes a cover with an access opening for collection of waste, and an insert for closing the drum, after the collection is completed.

b. Description of the Prior Art

There has been recent, wide-spread concern over the safe, and secure collection and proper disposal of hazardous waste materials in a large number of industries. Failure to safely collect and dispose hazardous materials have led a number of disasters which affected the environment, and the health and welfare of a large number of people. For example, in the health industry, and more specifically in hospitals and clinics, various items including paper towels, syringes, rubber gloves are disposed in large numbers on a daily basis. Frequently these items are hazardous because they may have been infected, or may contain organic material prone to spoilage. As a result, if these items are not collected and disposed properly, they can be the source of infections and may contribute in spreading diseases. This problem has been aggravated by the trend in the industry to use disposable items. Frequently some items (such as syringe needles, and rubber gloves) are disposed after a single use.

Although various methods and containers have been use for the above-mentioned purpose, none of these proved satisfactory. For example, frequently, a plastic bag is disposed in a garbage pail for collection of the waste material. After the bag is full, it is removed from the pail, closed with a bag tie, or other similar means. However sharp objects, such as syringe needles may puncture the bag causing injury and/or infection to the person carrying it, or to any one else coming in contact with the bag. In addition, the bag is then either thrown in a large container for collection with other refuse, or it is disposed in a container for further disposal. The container itself then must be sealed to insure that no one comes in contact with its contents.

Thus, previous methods were unsafe, and labor intensive.

OBJECTIVES AND SUMMARY OF THE INVENTION

In view of the above-mentioned disadvantages of the prior art, it is an objective of the present invention to provide a method for safe collection and disposition of hazardous waste.

A further objective is to provide a method for disposing waste which is easy and can be completed in a short period of time.

Yet another objective is to provide a waste collection assembly which is relatively inexpensive.

A further objective is to provide a waste collection assembly with which hazardous waste can be disposed safely, efficiently and economically.

Other objectives and advantages of the invention, shall become apparent from the following description of the invention. Briefly, an assembly for collecting and disposing hazardous waste constructed in accordance with this invention comprises a drum assembly comprising an enclosure with an access opening for collecting waste, and a separate replaceable insert which may be positioned inside the drum to cover the access opening. The assembly is placed at the collection site, with the insert removed from the enclosure. After collection of waste, the insert is positioned inside the drum to cover the access opening. The assembly may then be sealed for shipping and disposal. A plastic bag may be provided for holding the waste within the enclosure.

DETAILED DESCRIPTION OF THE INVENTION

Figure 5:
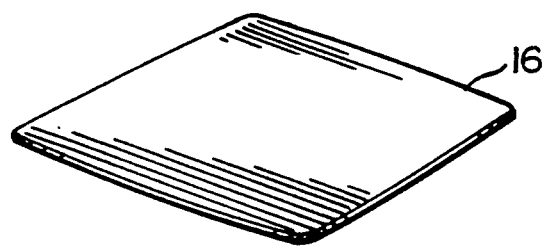
FIG. 5 shows a perspective view of an insert for the waste collection drum of FIG. 4.
Figure 6:
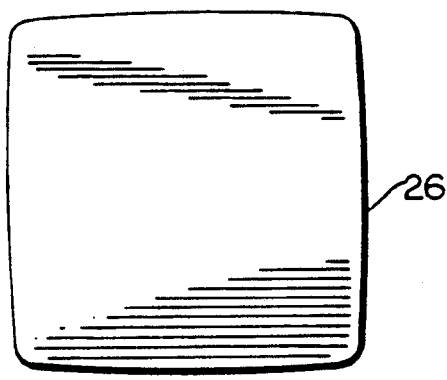
FIG. 6 shows a plan view of the insert of FIG. 5.
Figure 7:
FIG. 7 shows a side view of the insert of FIGS. 5 and 6.

Referring now to the drawings, a waste assembly constructed in accordance with this invention includes a drum body 12, a drum top 14, and an insert 16 (shown in detail FIGS. 5–7). Drum body 12 has a bottom 18 and a tubular body sidewall 20 extending upwardly from the bottom. The sidewall 20 is terminated by a top edge 22.

Drum top 14 has a flat member 24 and a top sidewall 26 extending downwardly from the flat member. The drum top and the drum body have generally complementary cross-sectional shapes and the drum top is slightly bigger in cross-sectional dimension than the drum body, so that the drum top can be inserted over the drum body in a telescopic engagement. In the Figures the drum body 12 and drum top 14 have a generally rectangular shape with rounded corners, however, these members may have other shapes such as square, round, oval, and so on.

Flat member 24 is provided with an access opening 28. This opening may be covered by a flap 30 having a sealing member 32 of the same shape as the opening 28 so that the flap can close the opening in an air-tight manner. The flap 30 preferably includes a securing member 34 for securing the flap to the drum top 14 as shown. The sealing member 32 is pivotable around a hinge line 36 for selectively opening and closing access opening 28 by the rotation of sealing member 32. Sealing member may be D-shaped, or may have other shapes. Preferably the flap is frangible along or adjacent to hinging line 36 so that the sealing member can be removed from the drum top 14. Alternatively, the flap 30 may be removably installed and secured to the drum top 14.

The waste assembly may also include a bag 38. The bag may be provided as part of a package by the manufacturer of the assembly, or it may be provided by the user.

As shown in FIGS. 5-7 insert 16 is generally a flat member having an outline substantially the same as the edge 22 of the drum body 12, and/or the top sidewall 26.

Drum body 12, top 14, and insert 16 may be made of any relatively stiff material to withstand rough handling, including fibers, plastic materials, cardboard, or sheet metal. Flap 30 can be made of the same, or different materials then the drum body, drum top or the insert. If made from the same material, the flap may be made integral with the drum top whereby the securing member may be omitted.

Figure 1:
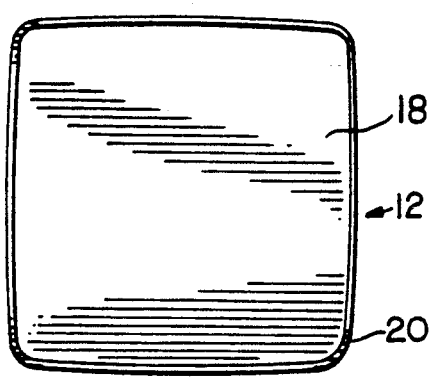
FIG. 1 shows a plan view of a drum body used in a hazardous waste assembly constructed in accordance with the invention.
Figure 2:
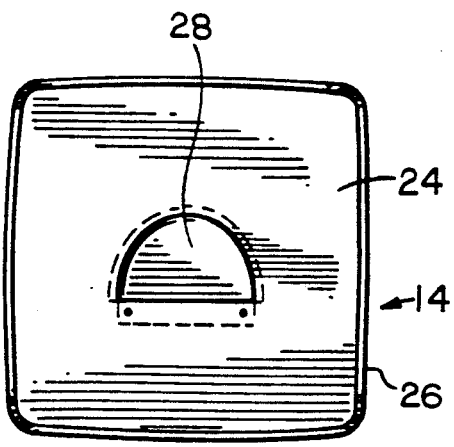
FIG. 2 shows a bottom view of a drum top for the body of FIG. 1.
Figure 3:
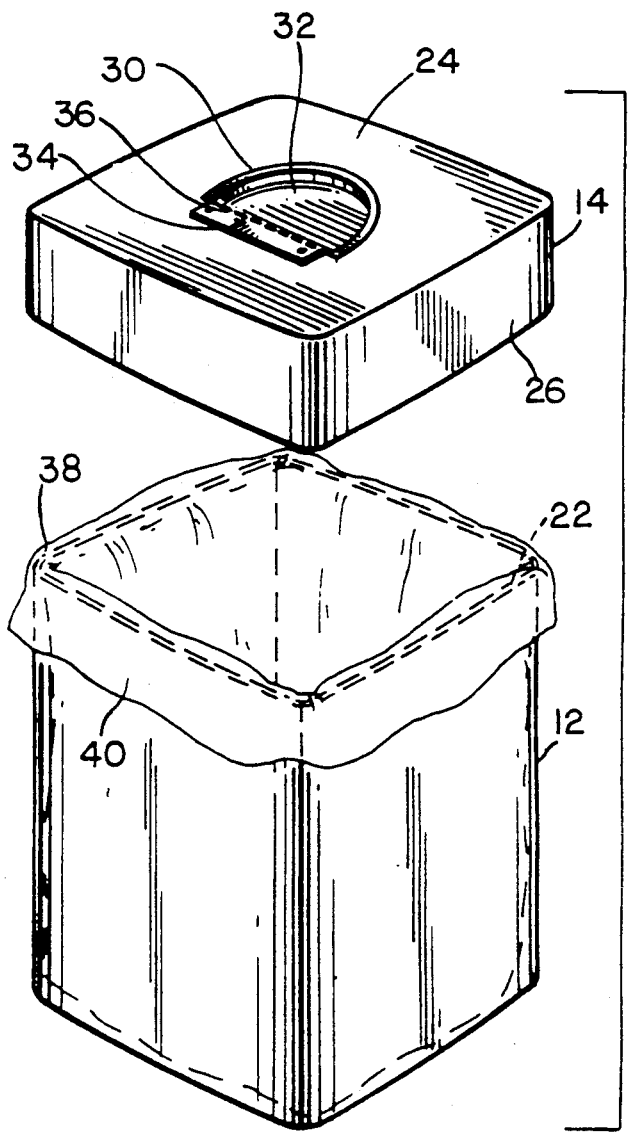
FIG. 3 shows a perspective view of the drum top being fitted over the drum body for collection of waste materials.
Figure 4:
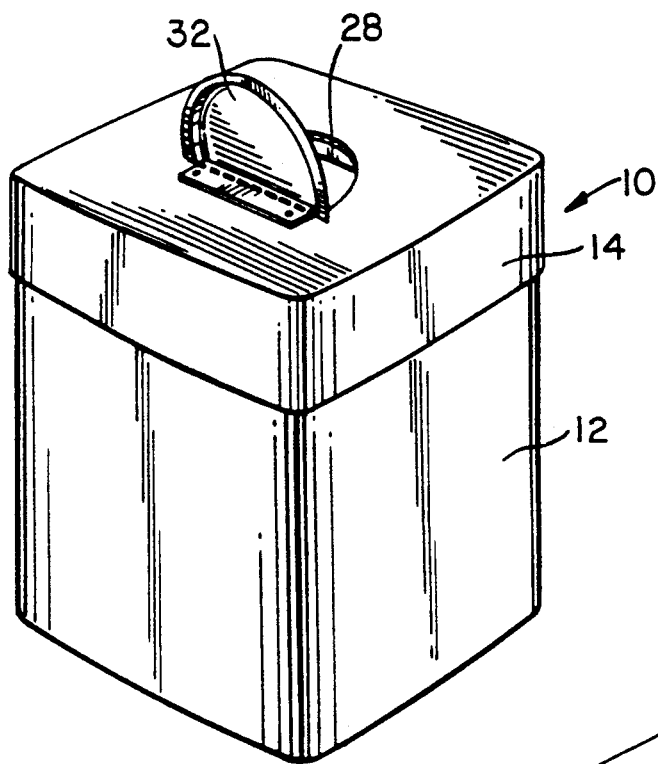
FIG. 4 shows a perspective view of the drum body and drum top assembled to form a waste collection drum.

The waste drum assembly may be used as follows. The insert (and optionally bag 38) may be disposed within the body 12 and the drum cover is temporarily secured to the drum body for shipping to the waste collection site. Alternatively, the different members of the assembly may be shipped separately. At the site, the drum top 14 is removed from the drum body, and the bag 38 is opened and expended within the body 12. The insert 16 is also removed, and is temporarily stored elsewhere. Alternatively, the insert 16 is secured either on the inside or on the outside of the drum (for example with a tape) in such a manner that it does not cover the access hole. Preferably, a bag is bigger than the drum body 12 at least vertically so that an upper portion of the bag 40 may be folded over edge 22 as shown in FIG. 3. The top 14 is positioned over the body 12 and is pushed down so that sidewalls 20 and 26 are telescopically engaged. Preferably the upper portion 40 of bag 38 is disposed between and frictionally engaged by the sidewalls 20, 26 so that the bag is maintained securely in the open position within the drum body 20. Thus a collection drum 10 is formed as illustrated in FIG. 4 in a relatively simple and efficient manner. The drum may be used for collecting hazardous waste material by opening flap 38 and dropping the waste material through opening 28. After each use, the flap is closed thereby keeping any odors from within the bag produced by various waste material from escaping through the opening 28.

Figures 8, 9:
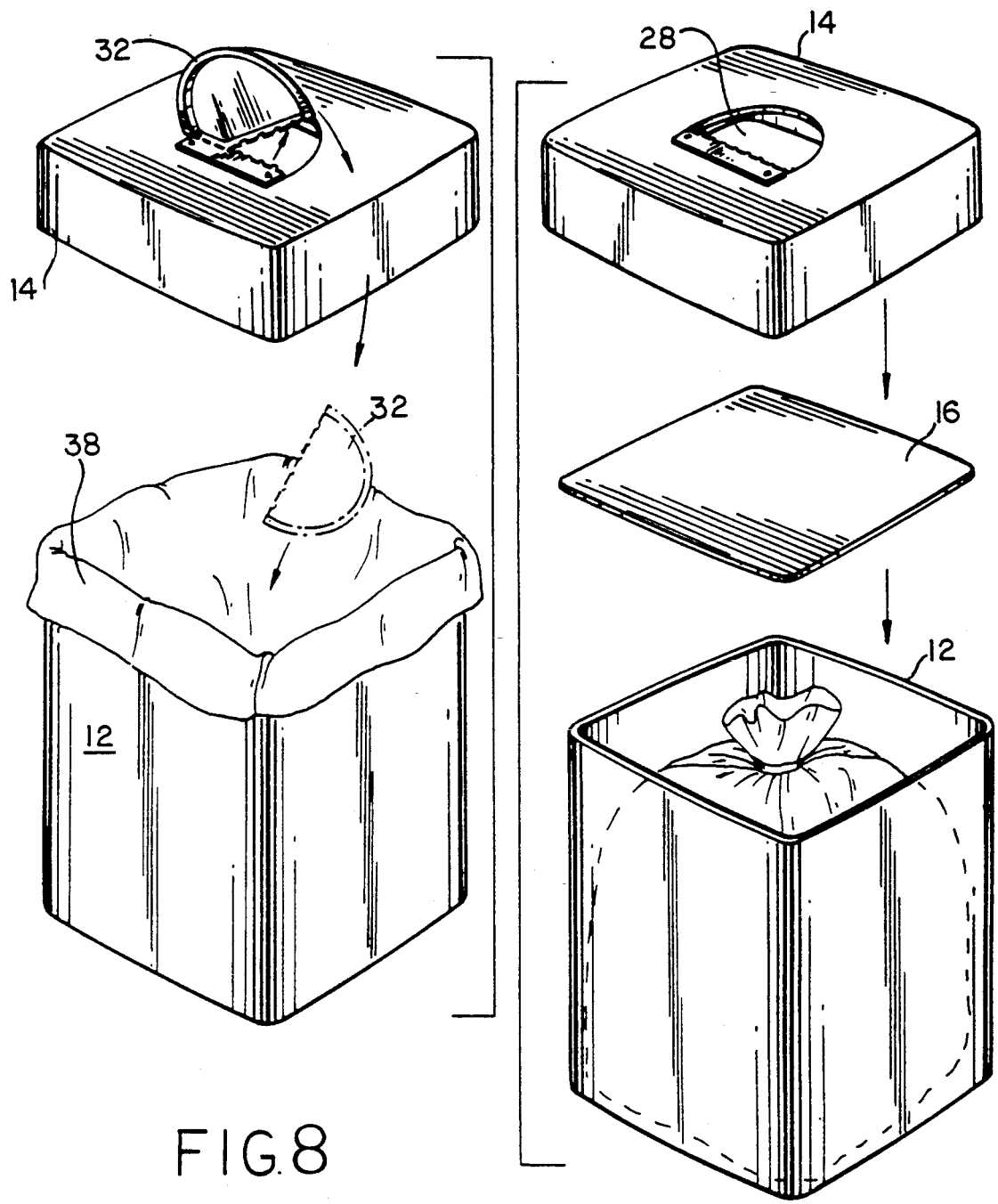
FIG. 8 shows a perspective view of the collection drum with the access flap being discarded.
FIG. 9 shows in perspective view the placement of the insert and closing of the drum.

Either at regular intervals, i.e. twice a day, at the end of shift, etc., or when the bag 38 is full, the drum 10 is closed and replaced by an empty drum. The full (or at least partially full) drum is closed as follows. Drum top 14 is removed from the body 12. The sealing member 32 (which may have been contaminated and is probably dirty from spillage) is broken away from the drum top 14 and thrown into the bag 38, as shown in FIG. 8. Alternatively, if the shape of the opening 28 permits, the sealing member 32 may be broken away and disposed in bag 38 before the top 14 is removed.

Figure 10:
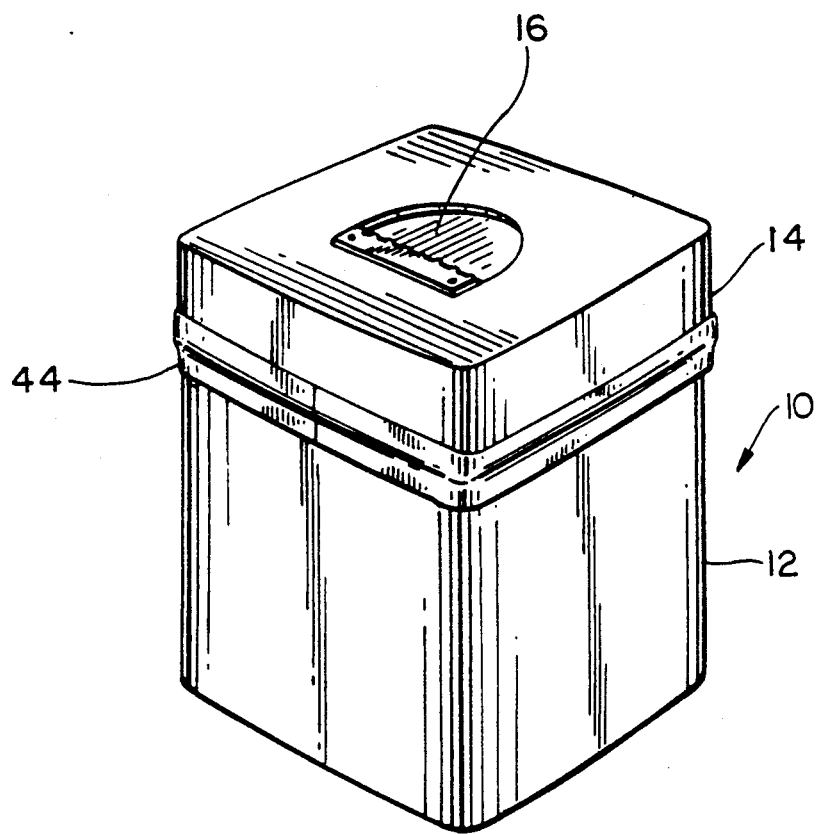
FIG. 10 shows a perspective view of a closed drum ready for disposal.

The bag 38 is closed with a tie 42, by applying a knot to the bag, or secured by other well-known means, as shown in FIG. 9. Then insert 16 is positioned over the edge 22, and drum top 14 is reinserted over the drum body 12, as shown in FIG. 9. This time, sidewalls 20, 26 are directly frictionally engaged, with insert 16 being captured between edge 22 and flat member 24, to form a closed drum 10' as shown in FIG. 10. In this configuration, opening 28 is closed off by insert 16. The closed drum 10' is now ready to be shipped to a disposal site. To insure that the closed drum does not open in transit, a tape 44 may be used to secure the drum to 14 and drum body 12 together. It should be appreciated that the resulting closed drum 10' is air-tight and capable of withstanding rough handling during shipping. In fact the closed drum may be made strong enough to meet the requirements of the Department of Transportation.

Obviously numerous modifications may be made to the invention without departing from its scope as defined in the appended claims.

I claim:

1. A waste drum assembly for the collection, shipping and disposal of medical waste comprising:
   a) a drum body having an interior and a tubular side wall having an upper end and being of predetermined length, a closed bottom and an open top, the top having a top edge defining in plan, a predetermined shaped peripheral outline;
   b) a removable top having a peripheral outline generally approximating the outline of the top edge and being removably mounted on the top of the drum body to close the drum body top, the removable top having an access opening therein for providing access to the interior of the drum body;
   c) a sealing member on the removable top closing the access opening in the removable top and being shiftable from a closed position at which it closes the access opening and an open position at which it opens the access opening wherein the sealing member is part of a flap hingedly connected to the removable top so that the sealing member pivots between its open and closed position, and wherein the flap is frangible so that the sealing member is adapted to be removed from the removable top and be placed in the drum body interior for disposal with the medical waste.
   d) an insert having a peripheral outline generally approximating the outline of the top edge and being removably mounted on the top of the drum body and being interposed between the removable top and the top edge and adapted to close off the interior of the drum body;
   e) whereby when the insert is removed medical waste is adapted to be inserted into the interior of the drum body through the access opening upon shifting the sealing means to its open position and when the insert is mounted on top of the drum body medical waste is adapted to be enclosed within the drum body interior for shipping and disposal.

2. The waste drum assembly of claim 1 wherein an open top bag having an upper peripheral portion is disposed within the interior of the drum body and possesses a length longer than the length of the drum body side wall so that the upper peripheral portion of the bag may be draped over the top edge and upper end of the drum body side wall.

3. The waste drum assembly of claim 1 wherein the drum body, removable top and insert are fiber.

4. The waste drum assembly of claim 1 the removable top comprises a substantially flat member adapter to rest on the top edge of the drum body, and a side wall downwardly depending from the flat member adapted to embrace the upper end of the drum body side wall.

5. The waste drum assembly of claim 1 wherein the insert is substantially flat.

6. The waste drum assembly of claim 1 wherein an open top bag having an upper peripheral portion is disposed within the interior of the drum body and possesses a length longer than the length of the drum body side wall so that the upper peripheral portion of the bag may be draped over the top edge and upper end of the drum body side wall; and wherein the drum body, removable top and insert are fiber; and wherein the removable top comprises a substantially flat member adapter to rest on the top edge of the drum body, and a side wall downwardly depending from the flat member adapted to embrace the upper end of the drum body side wall; and wherein the sealing member is part of a flap hingedly connected to the removable top so that the sealing member pivots between its open an closed position; and wherein the flap is frangible so that the sealing member is adapted to be removed from the removable top and be place in the drum body interior for disposal with the medical waste; and wherein the insert is substantially flat.

7. A waste drum assembly for the collection, shipping and disposal of medical waste comprising:
  a) a drum body having an interior and a tubular side wall having an upper end and being of predetermined length; a closed bottom and an open top, the top having a top edge defining in plan, a predetermined shaped peripheral outline;
  b) a removable top having a peripheral outline generally approximating the outline of the top edge and being mounted on the top of the drum body to cooperate in closing the drum body top, the removable top having an access opening therein having previously provided access to the interior of the drum body;
  c) a sealing member having previously closed the access opening in the removable top and having previously been shiftable from a closed position at which it closes the access opening and an open position at which it opened the access opening, the sealing member having been part of a flap hingedly connected to the removable top and being disposed in the interior of the drum body;
  d) an insert having a peripheral outline generally approximating the outline of the top edge and being mounted on the top of the drum body and interposed between the removable top and the top edge and held in place by the removable top for closing the top of the drum body and the interior of the drum body;
  e) an open top bag having an upper peripheral portion disposed within the interior of the drum body and possessing a length longer than the length of the drum body side wall so that the upper peripheral portion of the bag had previously been draped over the top edge and upper end of the drum body side wall to permit medical waste to be placed therein through the access opening when the sealing member was in the open position, medical waste and the sealing member being in the bag, the upper peripheral portion of the bag being tied shut;

whereby the waste drum assembly with contained medical waste in the tied shut bag in the drum body interior closed by the insert held in place by the removable top may be shipped for disposal.

8. The waste drum assembly of claim 7 wherein the removable top defines a juncture with the drum body side wall and sealing tape seals the juncture between the removable top and drum body side wall.

9. The waste drum assembly of claim 7 wherein the drum body, removable top and insert are fiber.

10. The waste drum assembly of claim 7 the removable top comprises a substantially flat member adapted to rest on the top edge of the drum body, and a side wall downwardly depending from the flat member adapted to embrace the upper end of the drum body side wall.

11. The waste drum assembly of claim 7 wherein the flap is frangible so that the sealing member is adapted to be removed from the removable top and be placed in the drum body interior for disposal with the medical waste.

12. The waste drum assembly of claim 7 wherein the insert is substantially flat.

13. The waste drum assembly of claim 7 wherein the removable top defines a juncture with the drum body side wall and sealing tape seals the juncture between the removable top and drum body side wall, the drum body, removable top and insert are fiber, the removable top comprises a substantially flat member adapted to rest on the top edge of the drum body, and a side wall downwardly depending from the flat member adapted to embrace the upper end of the drum body side wall, the flap is frangible so that the sealing member is adapted to be removed from the removable top and be placed in the drum body interior for disposal with the medical waste, the insert is substantially flat.

14. A method of collecting medical waste comprising the steps of:
  a) providing a waste drum assembly comprising:
    i) a drum body having an interior and a tubular side wall having an upper end and being of predetermined length, a closed bottom and an open top, the top having a top edge defining in plan, a predetermined shaped peripheral outline;
    ii) an open top bag having an upper peripheral portion disposed within the interior of the drum body and possessing a length longer than the length of the drum body side wall so that the upper peripheral portion of the bag is draped over the top edge and upper end of the drum body side wall;
    iii) a removable top having a peripheral outline generally approximating the outline of the top edge and being removably mounted on the top of the drum body to close the drum body top, the removable top having an access opening therein for providing access to the interior of the drum and the bag therein;
    iv) a sealing member on the removable top closing the access opening in the removable top and being shiftable from a closed position at which it closes the access opening and an upper position at which it opens the access opening;
  b) shifting the sealing member to its open position and placing the medical waste in the bag through the access opening;
  c) substantially filling the bag with medical waste;
  d) removing the removable top;

e) undraping the upper peripheral portion of the bag from the upper end of the drum body side wall and top edge:

f) tying the upper peripheral portion of the bag to tie shut the bag and contain the medical waste therein wherein the sealing member is removed from the removable top and placed in the bag before tying the upper peripheral portion thereof;

g) placing on the top edge an insert having a peripheral outline generally approximating the outline of the top edge to close off the interior of the drum body with the tied bag with medical waste therein;

h) placing the removable top on top of the drum body and over the insert to hold the insert in place and to cooperate in closing the drum body;

i) whereby the waste drum assembly with contained medical waste in the tied shut bag in the drum body interior closed by the insert held in place by the removable top may be shipped for disposal.

15. The method of collecting medical waste of claim 14 wherein sealing tape is applied to the juncture between the removable top and the drum body side wall.

16. The method of collecting medical waste of claim 14 wherein the sealing member is removed from the removable top and placed in the bag before tying the upper peripheral portion thereof, and sealing tape is applied to the juncture between the removable top and the drum body side wall.

* * * * *

UNITED STATES PATENT AND TRADEMARK OFFICE
CERTIFICATE OF CORRECTION

PATENT NO. : 5,328,028
DATED : July 12, 1994
INVENTOR(S) : James A. Hale, Jean Sawyer, John A. Plunkett, Lou A. Marinaccio It is certified that error appears in the above-indentified patent and that said Letters Patent is hereby corrected as shown below:

On the title page: Item [73] "Greif Bors. Corporation should read --Greif Bros. Corporation --.

Signed and Sealed this

Twenty-first Day of February, 1995

Attest:

BRUCE LEHMAN

Attesting Officer     Commissioner of Patents and Trademarks